United States Patent
Dasgupta et al.

(10) Patent No.: US 10,208,387 B2
(45) Date of Patent: Feb. 19, 2019

(54) THREE-ELECTRODE BUFFER GENERATOR AND METHOD

(71) Applicants: Board of Regents, The University of Texas System, Austin, TX (US); Dionex Corporation, Sunnyvale, CA (US)

(72) Inventors: Purnendu K. Dasgupta, Arlington, TX (US); Yongjing Chen, Sunnyvale, CA (US); Kannan Srinivasan, Tracy, CA (US)

(73) Assignees: Board of Regents, The University of Texas System, Austin, TX (US); Dionex Corporation, Sunnyvale, CA (US)

( * ) Notice: Subject to any disclaimer, the term of this patent is extended or adjusted under 35 U.S.C. 154(b) by 0 days.

(21) Appl. No.: 15/415,700

(22) Filed: Jan. 25, 2017

(65) Prior Publication Data

US 2017/0130345 A1    May 11, 2017

Related U.S. Application Data

(62) Division of application No. 13/593,441, filed on Aug. 23, 2012, now Pat. No. 9,580,822.

(Continued)

(51) Int. Cl.
*C25B 7/00* (2006.01)
*B01D 61/44* (2006.01)
(Continued)

(52) U.S. Cl.
CPC .............. *C25B 7/00* (2013.01); *B01D 15/168* (2013.01); *B01D 61/44* (2013.01); *B01D 61/445* (2013.01);
(Continued)

(58) Field of Classification Search
CPC ........ C25B 7/00; G01N 30/34; B01D 15/168; B01D 61/42; B01D 61/44; B01D 61/445; B01D 61/46
See application file for complete search history.

(56) References Cited

U.S. PATENT DOCUMENTS 3,239,442 A    3/1966 Tirrell
3,341,299 A    9/1967 Catravas
(Continued)

FOREIGN PATENT DOCUMENTS

EP    1897601 A1    12/2008
KR    10-2005-0020298    3/2005
(Continued)

OTHER PUBLICATIONS

Page 207 of a faculty publication of the National Cheng Kung University, published in 1983.
(Continued)

*Primary Examiner* — Steven A. Friday
(74) *Attorney, Agent, or Firm* — Morgan, Lewis & Bockius LLP

(57) ABSTRACT

An electrodialytic buffer generator is described. The buffer generator may include a central buffer-generating channel having an inlet and outlet, a second chamber, and a third chamber. The buffer-generating channel, the second chamber, and the third chamber may each include an electrode. The buffer generator may also include a first ion exchange barrier and a second ion exchange barrier. The first ion exchange barrier can be disposed between the second chamber and the buffer-generating channel. The second ion exchange barrier can be disposed between the third chamber and the buffer-generating channel.

17 Claims, 11 Drawing Sheets

Related U.S. Application Data

(60) Provisional application No. 61/528,127, filed on Aug. 26, 2011, provisional application No. 61/526,592, filed on Aug. 23, 2011.

(51) Int. Cl.
*G01N 30/34* (2006.01)
*B01D 61/46* (2006.01)
*B01D 15/16* (2006.01)
*G01N 30/06* (2006.01)

(52) U.S. Cl.
CPC .......... *B01D 61/46* (2013.01); *B01D 2311/18* (2013.01); *B01D 2311/2653* (2013.01); *G01N 30/34* (2013.01)

(56) References Cited

U.S. PATENT DOCUMENTS

| | | | |
|---|---|---|---|
| 4,459,357 A | 7/1984 | Jansen et al. | |
| 4,671,863 A | 6/1987 | Tejeda | |
| 4,936,962 A | 6/1990 | Hatzidimitriu | |
| 4,999,098 A | 3/1991 | Pohl et al. | |
| 5,045,204 A | 9/1991 | Dasgupta et al. | |
| 5,316,680 A | 5/1994 | Frechet et al. | |
| 5,730,867 A | 3/1998 | Drew et al. | |
| 6,129,832 A * | 10/2000 | Fuhr | G05D 21/02 204/400 |
| 2001/0023825 A1 * | 9/2001 | Frumin | G01N 27/44773 204/458 |
| 2003/0019753 A1 * | 1/2003 | Ogle | B01D 57/02 204/548 |
| 2003/0132163 A1 | 7/2003 | Srinivasan et al. | |
| 2003/0226752 A1 * | 12/2003 | Vigh | B01D 57/02 204/450 |
| 2004/0149581 A1 | 8/2004 | Srinivasan et al. | |
| 2004/0195100 A1 | 10/2004 | Srinivasan et al. | |
| 2005/0082228 A1 | 4/2005 | De Lamotte | |
| 2006/0266650 A1 | 11/2006 | Han | |
| 2007/0138015 A1 * | 6/2007 | Bukshpan | G01N 27/44747 204/548 |
| 2009/0178928 A1 | 7/2009 | Groos et al. | |
| 2011/0198225 A1 * | 8/2011 | Kim | B01D 57/02 204/452 |
| 2012/0031763 A1 | 2/2012 | Ohmi et al. | |

FOREIGN PATENT DOCUMENTS

| | | |
|---|---|---|
| WO | WO 9951529 A1 | 10/1999 |
| WO | WO 2010019402 A1 | 2/2010 |
| WO | WO 2010122989 A1 | 10/2010 |
| WO | WO 2011037530 A1 | 3/2011 |
| WO | WO 2012073566 A1 | 6/2012 |

OTHER PUBLICATIONS

Chen et al., "Electrodialytic Membrane Suppressors for Ion Chromatography Make Programmable Buffer Generators," Anal. Chem., 2012, 84, 67-75 and 12 pages of supporting information and 24 pages Excel spreadsheet.

Chen et al., "pH- and Concentration-Programmable Electrodialytic Buffer Generator," Anal. Chem., 2012, 84, 59-66 and 22 pages of supporting information.

Ohira et al., Electrodialytic Ion Isolation for Matrix Removal, Anal. Chem., 2012, 84, 5421-5426.

Kielland et al., Individual Activity Coefficients of Ions in Aqueous Solutions, J. Amer. Chem. Soc., 1937, 59, 1675-1678.

* cited by examiner

THREE-ELECTRODE BUFFER GENERATOR AND METHOD

CROSS-REFERENCE TO RELATED APPLICATIONS

This application is a divisional patent application of U.S. patent application Ser. No. 13/593,441, filed Aug. 23, 2012, which claims the benefit of U.S. Provisional Patent Application No. 61/526,592, filed Aug. 23, 2011 and U.S. Provisional Patent Application No. 61/528,127, filed Aug. 26, 2011, each of which is incorporated by reference in its entirety for all purposes.

BACKGROUND

Buffers are widely used for pH control of chemical processes. A buffered solution resists changes in pH when acids or bases are added or when dilution occurs. Biochemists are particularly concerned with buffers because the proper functioning of any biological system depends on pH. The rate of one particular enzyme-catalyzed reaction varies with pH. For an organism to survive, pH of each subcellular compartment has to be precisely controlled so that each reaction proceeds at the proper rate. The majority of biological samples that are used in research are made in buffers, such as phosphate, Tris-HCl at pH around 7.

Microbial fuel cells (MFCs), which can directly generate electricity from biodegradable substance, have rapidly gained increasing research attention. Microbes oxidize organic substrates to supply electrons to the anode; the electrons then travel through an external circuit to the cathode and participate in reduction reactions. Associated with these reactions is the generation of $H^+$ and $OH^-$ from water electrolysis in the analyte and catholyte, respectively, which creates a pH imbalance in system. Since the pH imbalance produces a 0.059 V/pH potential loss, minimizing the pH imbalance is necessary for maximizing the power densities. Phosphate buffers are usually used to stabilize the pH and reduce the internal resistance, which in turn enhances the system performance. In order to have a sufficient supply of protons in a cathode compartment, a high concentration of buffer is needed, and over time it might still become depleted. A stable supply of fresh buffer will be attractive.

Buffers are of wide utility in analytical chemistry as well. Reversed-phase high performance liquid chromatography (RP-HPLC) has always been a very powerful tool for organic compound analysis, especially biological sample analysis. Buffers like phosphate or acetate are widely employed in the mobile phase in the analysis of ionizable compounds. Because the retention of ionizable acid/base compounds has a strong dependence of their degree of ionization, a correctly chosen buffer pH will ensure that the ionizable functional group is in a single form, whether ionic or neutral. When developing a rugged method, it is desirable to select a mobile phase with a final pH at least one pH unit away from any analyte's pK value to cause ionization or suppression of the analytes. Slight variations in pH can have a dramatic impact on separation, in terms of selectivity, capacity factor, peak shape, resolution and reproducibility. An improper pH for ionizable analytes often leads to asymmetric peaks that are broad, tail, split or shoulder. And sharp, symmetrical peaks are necessary in quantitative analysis in order to achieve low detection limits, low relative standard deviations between injections, and reproducible retention times. Even in the analysis of non-ionizable compounds, it is often equally important to control pH when working with field samples in the presence of ionizable contaminants or impurities so as to eliminate the interference of undesirable peaks. If the sample solution is at a pH damaging to the column, the buffer will quickly bring the pH of the injected solution to a less harmful pH. Another technique of RP-HPLC, ion-pair chromatography (IPC) also requires precise control of pH in the mobile phase, because variation of pH in the mobile phase can introduce large changes in the degree of ionization of not only the solutes but also the ion-pairing reagent. In practice, a chromatographer usually measure the pH of the buffer additives before mixing it with other solvents, but the pKa values of the acids used to prepare the buffers change with the solvent composition (and each in a different degree), and so does the pH of the buffer. Sometimes, the pH is measured after mixing the buffer with the organic modifier; even in this instance, the potentiometric system is usually calibrated with aqueous standards, and the measured pH is not the true pH of the mobile phase. Theoretically, a chromatographer can estimate the concentration of buffer needed to achieve a desired pH for separation based on calculation from equations. However, in reality pH can vary significantly from those calculations. Therefore the analyst has to experimentally determine and report the value for the mobile phase pH with a calibrated pH meter to ensure reproducibility results. When developing a method, the analyst might have to adjust the mobile phase many times before it reaches the optimum condition. With one stock buffer solution, the final concentration of buffer can only be varied by varying the ratio of buffer to the organic solvent, which largely limits the flexibility of the optimization process. To make different buffer stock solutions is tedious and time-consuming. If the buffer concentration can be varied simply by varying the applied current, it will provide a much efficient way and reduce lots of waste solvents.

pH-based separation of proteins with ion-exchange chromatography is another chromatographic technique that relies on buffers. Initially it employs nearly linear pH gradients generated from mobile phase (ampholyte buffers) and stationary phase (weak anion-exchange column) to elute proteins in the order of their pI, and was termed "chromatofocusing". More recently, the technique was developed into "gradient chromatofocusing", which employs common buffers with low molecular mass instead of polymeric ampholytes. There are two types of gradients; a pH gradient in time at column outlet causing differential elution of proteins and a pH gradient in distance within the column affecting the focusing of the protein bands. HPLC gradient pumps are typically used to generate the linear pH gradient in time by varying the ratio of high-pH buffer and low-pH buffer, which are mixtures of buffer components with pKa values approximately equally spaced throughout the gradient pH range.

Capillary electrophoresis (CE) is another powerful separation tool for analysis of proteins and peptides, as well as drug enantiomers. Its unprecedented resolution allowing separation of species with very subtle differences in structure is a consequence of its extremely high efficiency, which, to some extent, depends on the running buffers it employs. Manipulation of buffer pH is usually a key strategy to optimize a separation, since buffer pH not only determines the extent of ionization of each individual analyte, but also strongly influences the charge of the capillary wall surface and the zeta potential, consequently affects both electrophoretic and electroosmotic velocities. Electrolysis of water is one of the most significant reactions occurring at the inlet and outlet vials in a CE experiment, the resulting $H^+$ and OH⁻ can change the pH in the vials. Thus, to successfully maintain the pH of the buffer, large vials should be used and the buffer must have adequate buffering capacity to neutralize the $H^+$ and $OH^-$ produced, and the buffer vials should be replenished regularly. By manipulating the running buffers, sample pre-concentration can also be achieved to overcome the drawback of limited sensitivity in CE.

Essentially a buffer is a mixture of an acid and its conjugate base. There must be comparable amounts of the conjugate acid and base (say, within a factor of 10) to exert significant buffering. The most common way to prepare a buffer solution is to decide the ratio of the conjugate acid-base pair based on Henderson-Hasselbalch equation, and weigh out the two components separately to obtain the desired ratio and then dissolve in water. An alternative is to weigh out one of the component, and produce the other component by a specified amount of strong acid or strong base to yield the desired ratio. Although it is a common practice to adjust pH of certain buffer solution with concentrated strong acid or base, it is easy to overshoot by adding too much of the titrants and have to make another solution and start over again.

SUMMARY

An electrodialytic buffer generator includes a flow-through central buffer-generating channel comprising a first electrode, having an inlet and an outlet; a second chamber comprising a second electrode; a third chamber comprising a third electrode; a cation exchange barrier, capable of passing cations but not anions and of blocking bulk liquid flow, disposed between the second chamber and the buffer-generating channel; and an anion exchange barrier, capable of passing anions but not cations and of blocking bulk liquid flow, disposed between the third chamber and the buffer-generating channel.

The generator may also include an aqueous cation source electrolyte solution in fluid communication with an inlet of the second chamber, and an aqueous anion source electrolyte solution in fluid communication with an inlet of the third chamber. In an embodiment, the generator may also include an electrolyte solution in fluid communication with the buffer-generating channel inlet. Additionally, the generator may include a first current source connected to the first and second electrodes, and a second current source connected to the second and third electrodes.

In an embodiment, the first electrode is grounded. Alternatively, the second and third electrodes are grounded. Optionally, a degassing device can be in fluid communication with the outlet of the buffer-generating channel.

An electrodialytic method for using the above buffer generator includes flowing a first aqueous solution into the flow-through central buffer-generating channel, where at least one of the first, second, or third aqueous solutions comprises an aqueous electrolyte solution that includes anions or cations, or both; passing a first current between the first and second electrodes; and passing a second current between the first and third electrodes, whereby a buffer solution is generated in the buffer-generating channel.

The first current may greater than the second current or alternatively the second current may be greater than the first current. The aqueous electrolyte solution may include a strong base salt of a multiprotic acid or a strong acid salt of a multiprotic base. The method may further include introducing the aqueous electrolyte solution into an inlet of at least one of the second or third chambers. The first aqueous solution can be deionized water or alternatively include an electrolyte solution. The method may further include introducing a deionized water into an inlet of at least one of the second or third chambers. In an embodiment, the aqueous solution may not be static and flow through the second and third chambers, where each chamber includes an inlet and an outlet.

The method can include outputting the buffer from the buffer-generating channel with a modified pH by changing a magnitude of the first current. The modified pH can include a gradient pH where the first current is changed as a function of time and the method further includes holding the second current to be approximately constant as a function of time causing the outputted buffer to have an approximately constant total buffer concentration. The method can also include outputting the buffer from the buffer-generating channel with a modified buffer concentration by changing a magnitude of the second current. The modified buffer concentration can be a gradient buffer concentration where the second current is changed as a function of time.

The method may also include degassing the generated buffer solution with a gas removal device.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION

Figure 1:
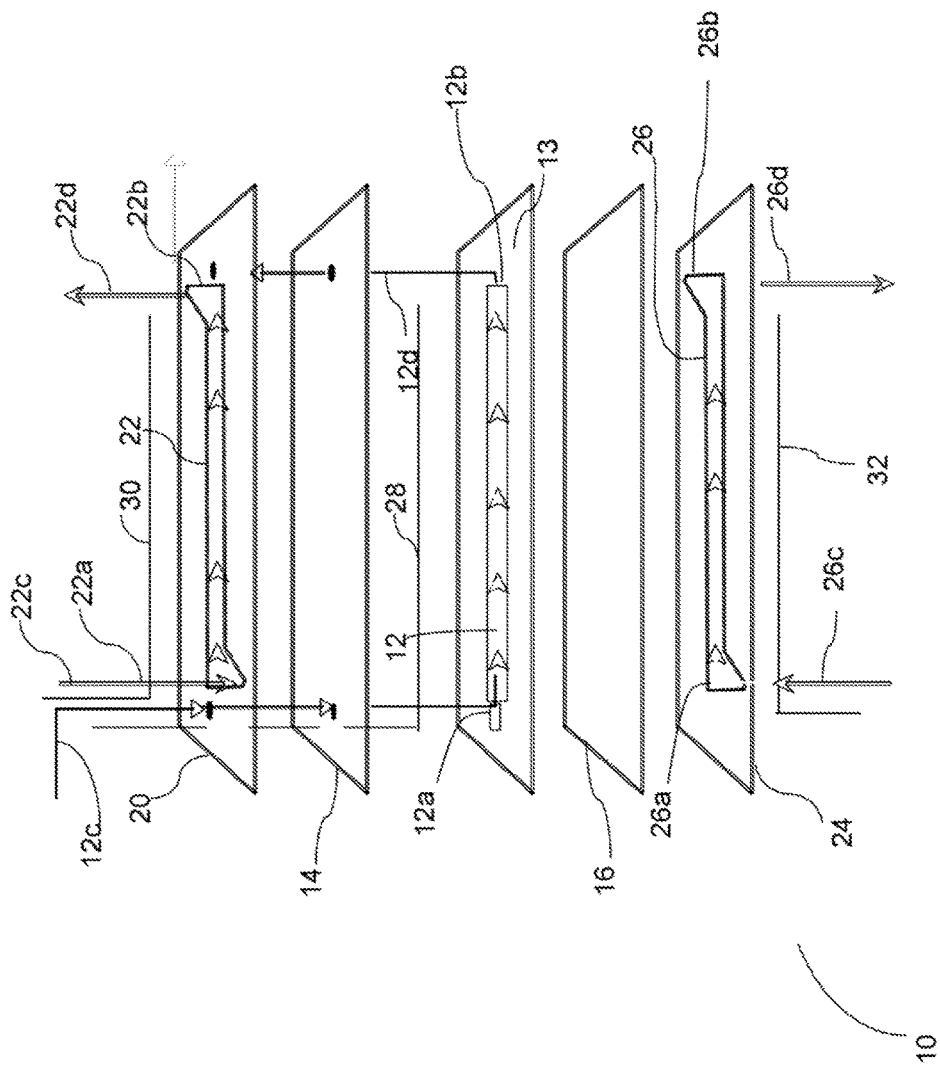
FIG. 1 is a schematic representation of one embodiment of the buffer generator.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

An electrodialytic buffer generator and methods of electrodialytically generating a buffer using the generator are described. The generator includes a flow-through central buffer-generating channel including a first electrode, having an inlet and an outlet; a flow-through second channel including a second electrode, having an inlet and an outlet; a flow-through third channel including a third electrode, having an inlet and an outlet; a cation exchange barrier, capable of passing cations but not anions and of blocking bulk liquid flow, disposed between the second channel and the buffer-generating channel; and an anion exchange barrier, capable of passing anions but not cations and of blocking bulk liquid flow, disposed between the third channel and the buffer-generating channel. In one embodiment the first electrode is grounded.

In an alternative embodiment, second and third channels can be replaced with a second and third chamber. The chambers are each configured to hold a static solution and are substantially non-flowing when generating a buffer.

If the electrode polarities are reversed, the central channel effluent would effectively be deionized dependent on the applied voltage and the current generated. The embodiments described herein combine electrodialytical generation of a user-chosen electrolyte $A^+Y^-$ and electrolytic generation of $H^+$ or $OH^-$ to electrodialytically generate a buffer. Electrolytic generation or consumption of $H^+$ or $OH^-$ has been demonstrated in the application of electrochemical pH. During electrodialytic buffer generation current flows between the first and second electrodes across the CEM and between the first and third electrodes across the AEM barrier. The current flowing through the first and second electrodes across CEM is referred to as "CEM current" while the current flowing through the first and third electrodes across AEM is referred to as "AEM current". With the CEM side bearing $A^+B^-$ held positive and the AEM side bearing $X^+Y^-$ held negative, with respect to a grounded electrode in the center channel, the device can be operated in such a way that excess amount of $H^+$ or $OH^-$ can be generated as a result of water electrolysis if the CEM current is larger or smaller than AEM current, respectively.

Referring again to FIG. 1, the buffer generator 10 includes a flow-through central buffer-generating channel 12 having an inlet 12a and an outlet 12b defined by gasket 13. An optional charged or uncharged screen, not shown, is disposed in channel 12 which can be similar to and serves a similar function to the screen of FIGS. 1-3 of U.S. Pat. No. 4,999,098 (the '098 patent) assigned to the Applicants of the instant specification. A cation exchange barrier in the form of cation exchange membrane (CEM) sheet 14 is mounted along one side of channel 12 extending along the flow direction through channel 12. An anion exchange barrier in the form of anion exchange membrane (AEM) sheet 16 is spaced from CEM 14 and together with CEM 14 forms opposed walls of channel 12 along the flow path through channel 12. CEM 14 and AEM 16 may be of the same type as the membrane sheets of FIGS. 1-3 of the '098 patent except they are of opposite charge, positive or negative. CEM 14 includes exchangeable cations and is capable of passing cations but not anions, and AEM 16 includes exchangeable anions and is capable of passing anions but not cations. They both block bulk liquid flow; that is, they block liquid flow except for possible insignificant leakage. Although ion-exchange membranes are preferred forms of the barriers, other barriers which accomplish these functions could be used.

A gasket 20 is mounted to the facing surface of CEM 14 defining a flow-through channel 22 having an inlet 22a and an outlet 22b. A gasket 24 is mounted to facing AEM 16 defining a flow-through anode channel 26 having an inlet 26a and outlet 26b. As illustrated, the flow-through central channel 12 is in the same direction as the flow-through channels 12, 20 and 26. However, the flow in any of the channels can be reversed. Electrode 28, illustrated in the form of a platinum wire, is disposed in central channel 12; electrode 30 is disposed in channel 22, and electrode 32 is disposed in channel 26. As illustrated, electrode 28 is grounded. Alternative forms of electrode could also be used such as flat bed electrodes of the '098 patent. Also, optional charged or uncharged screens or resin particles or a monolith, not shown, may be disposed in channels 12, 22 and 26 of the foregoing type.

In one embodiment, an aqueous cation source electrolyte solution from a source, not shown, flows in line 22c to inlet 22a, through channel 22 and out outlet 22b in line 22d. An aqueous anion source electrolyte solution from a source, not shown, flows in line 26c to inlet 26a, through channel 26 and out outlet 26b through line 26d. Also, an aqueous liquid, preferably deionized water, from a source not shown, flows through line 12c to inlet 12a, through central channel 12 and out outlet 12b through line 12d. As used herein, the terms "cation" and "anion" exclude the hydrogen and hydroxide ions produced during electrolysis of water.

External support blocks, not shown, of the type described in the '098 patent may be used to enclose channels 22 and 26 and to provide internal support for generator 10.

Figure 2A:
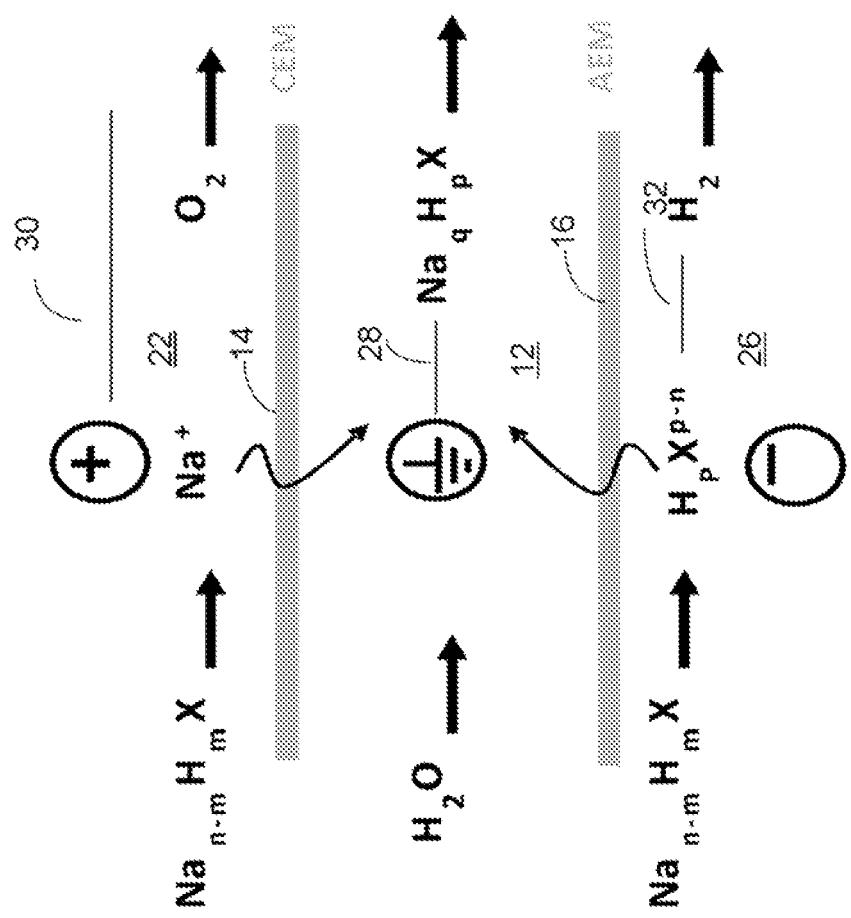
FIG. 2(a) and FIG. 2(b) schematically illustrate reaction schemes using the buffer generator of FIG. 1 in which water is fed to the buffer-generating channel and electrolyte is fed to the outside channels.

FIG. 2(a) illustrates a reaction scheme for one embodiment using the device of FIG. 1 using a strong base of a multiprotic base in an aqueous feed solution for anode channel 22 and cathode channel 26. Deionized water is the solution fed to central channel 12. In one embodiment, $Na_{n-m}H_mX$, flowing in channels 22 and 26, includes an aqueous solution of $Na_2HPO_4$ wherein n-m equals 2 and m equals 1. Note that X represents an anionic species and $Na_2HPO_4$ represents an example of a strong base salt. Current passes from a first current or power source, not shown, between positive electrode 30 (anode) and grounded electrode 28 (the CEM current) while a second current passes from a second current or power source, not shown, between negative electrode 32 (cathode) and grounded electrode 28 (the AEM current). $Na^+$ ions pass through CEM 14 under the influence of the CEM current. $Na_{n-m}H_mX$ is converted to $Na^+$, $H^+$, $HPO_4^{2-}$, $O_2$ and $H_2O$ during electrolysis in channel 22. $Na_{n-m}H_mX$ ($Na_2HPO_4$) also flows through channel 26. $H_pX^{p-n}$ ($HPO_4^{2-}$) passes through AEM 16 under the influence of the AEM current. $Na_2HPO_4$ is converted to $Na^+$, $OH^+$, $HPO_4^{2-}$, $H_2$, $H_2O$ in channel 26. In the central buffer-generating channel 12, the $Na^+$ and $HPO_4^{2-}$ ions are converted to a $Na^+$, $H_2PO_4$, and $HPO_4^{2-}$ in a buffer solution. Electrolysis takes place in all three channels. The reactions for this buffer-generating system are illustrated in more detail in FIGS. 3(a) and 3(b) described below. Note that B represents a cation that can migrate across the cation exchange membrane such as, for example, $H^+$, $Na^+$, or $K^+$. In addition, Y represents an anionic species that can migrate across the anion exchange membrane such as, for example, $OH^-$, $PO_4^{3-}$, $HPO_4^{2-}$, or $H_2PO_4^{1-}$. Suitable other feed solutions include phosphate, citrate, borate, tris, and ethylenediamine and the like and combinations thereof. Suitable buffer solutions produced from these feed solutions include $NaH_2PO_4Na_2PO_4$; $NaH_2PO_4$-phosphoric acid; Citric acid-Sodium Citrate; Boric acid-Borate; Tris-Tris HCL and ethylenediamine-ethylenediamine acid (HCl) and the like and combinations thereof.

Figure 2B:
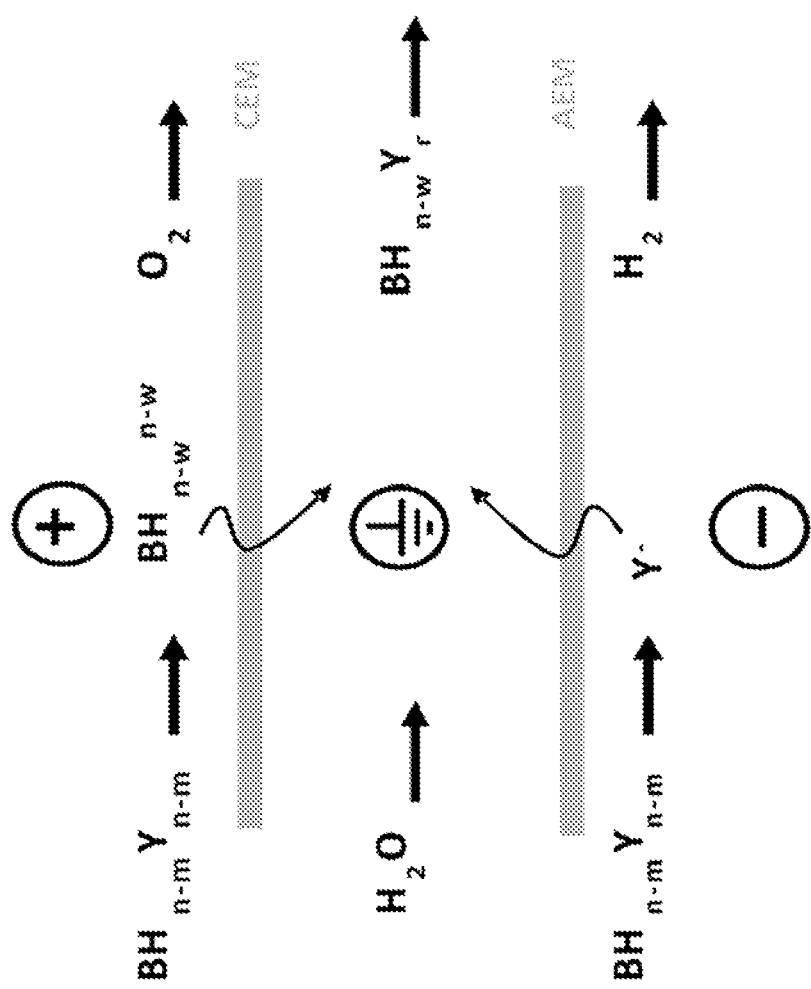

FIG. 2(b) illustrates the same apparatus used to generate an aqueous buffer solution using a strong acid salt of a multiprotic base solution as the feed solution. An example of a strong acid salt can be $NaH_2H_2PO_4$. Suitable feed solutions include sodium phosphate dibasic, sodium phosphate mono basic, sodium phosphate, and sodium bicarbonate, sodium carbonate and the like and combinations thereof. Suitable buffer solutions produced by this system include $NaH_2PO_4$—$Na_2HPO_4$; $NaH_2PO_4$—$Na_2PO_4$; $NaH_2PO_4$-$H_3PO_4$, and $Na_2CO_3$—$NaHCO_3$ and the like and combinations thereof.

The pH of the buffer preferably is within ±1 pH unit from the pKa of the buffer component. The buffer pH range may be in the pH 0 to 14 regime and more preferably in the pH 2 to 10 regime. The buffer concentration is preferably in the 0.001 M to 1 M and more preferably in the 0.005 to 0.1 M and most preferably in the 0.005 to 0.05M.

The CEM and AEM current controls the amount of cations and anions, respectively, transported into or from the central channel 12. The difference between the CEM current and AEM current determines the amount of the generated $H^+$ or $OH^-$ to achieve the desired pH of the generated buffer solution.

As illustrated in FIGS. 2(a) and 2(b), electrode 28 is grounded and forms one of the electrodes in the electrode pairs with electrodes 30 and 32, respectively, for application of the different CEM and AEM currents. By using the two variable power sources, the CEM current may be controlled to be greater than, less than, or equal to the AEM current. Here, electrode 30 is connected to the positive terminal of the power supply and electrode 32 is connected to the negative terminal of a second power source with a common ground connection.

In an alternative to using a grounded electrode 28 is to use three power supplies where the counter electrode for each one of them is the common ground. Electrode 30 is connected for example to the positive terminal on a first power supply; electrode 32 is connected to the negative terminal of a second power supply, and electrode 28 is connected to the negative terminal of a third power supply. Each power supply is grounded. In this configuration the potentials are arranged in such a manner to facilitate a potential drop that would allow transport of ions from and/or to the central product channel. Therefore it does not mandate the need to ground the central product channel. In the reversed mode of operation where the polarity is reversed the outer channels may be grounded or the potential of the electrodes can be arranged in such a manner to facilitate transport of ions.

Many modifications of the foregoing first embodiment of FIG. 1 of the three-electrode buffer generator are within the scope of the invention. In one alternative, the aqueous solution in channels 22 and 26 which are flow-through channels in the first embodiment may be replaced by large stationary or non-flowing reservoirs such as of the type disclosed in U.S. Pat. No. 6,225,129 as the ion source reservoirs.

In another embodiment, the outer electrode polarities are reversed. In this case, ion flow across the membranes is from electrode 12 in channel 12 (referred to as the "reverse polarity embodiment") through barriers 14 and 16 towards electrodes 30 and 32 in channels 22 and 26, respectively, instead of the opposite direction as in the first embodiment. In this embodiment, the aqueous solution flowing through channel 12 includes an electrolyte solution including cations, anions or both. Here, in contrast to the first embodiment, cations or anions are removed from channel 12 to produce the desired buffer solution instead of being added to it as in the first embodiment.

Figure 7:
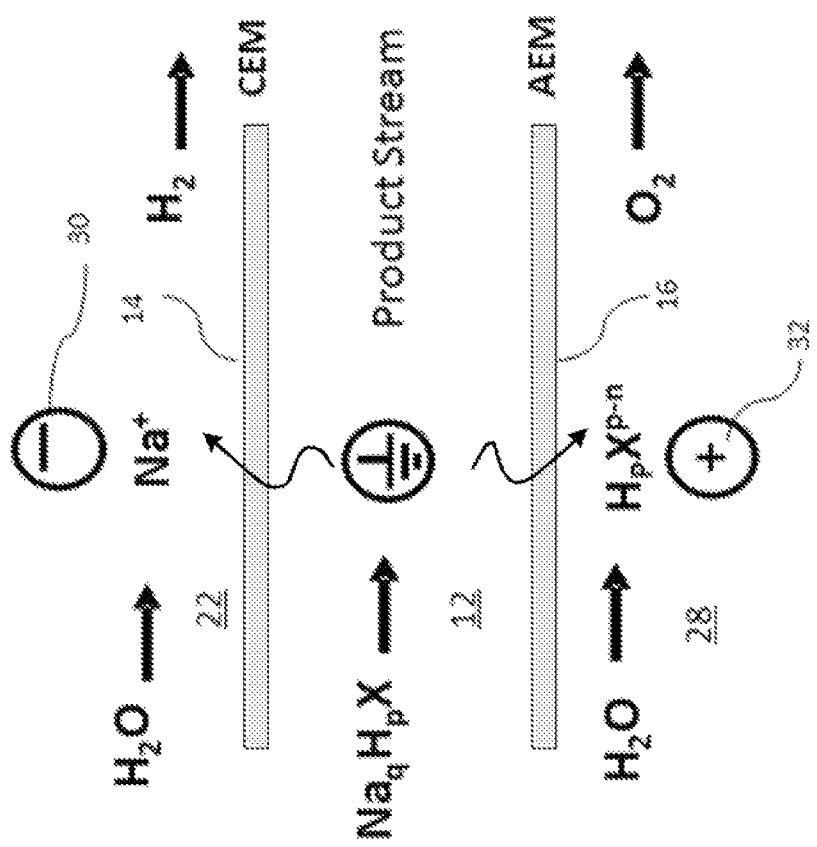
FIG. 7 is a schematic representation of a reversed polarity form of a buffer generator.

The reversed polarity embodiment is illustrated schematically in FIG. 7. The device behaves like a deionizer allowing cations to migrate via CEM membrane 14 towards cathode 30 and the anions to migrate via the AEM 16 toward anode 32. The source stream including the ions that would be useful to make the buffer is pumped into the central channel 12. Deionized water stream is pumped into channels 22 and 28. Upon applying a potential between channels 22, 28 and central channel 12, electrolysis occurs resulting in production of hydronium ions and hydroxide ions on the surface of the anode and cathode electrodes 32 and 30, respectively. The transport of the anions and cations allow for control of the pH and the ionic strength of the influent source stream. For example, if $Na_2HPO_4$ is introduced into central channel 12 when the electrodes are powered in cathode channel 30 and central channel 12, the sodium ions are removed via CEM 14. When a current is applied between the anode channel 28 and the central channel 12, the $HPO_4^{2-}$ anion would also be removed via AEM 16. This setup could be used to make a buffer including $Na_2HPO_4$ and $NaH_2PO_4$. By altering the applied currents a pH gradient and/or a gradient in concentration could be easily achieved. It should be noted that in the present setup the device behaves like a deionizing unit, and no addition of ions are possible as in the normal polarity setups discussed in the previous embodiments.

In another embodiment, electrode 28 is an ungrounded electrode and electrodes 30 and 32 are grounded. A grounded electrode can be an electrode having a potential of zero with no polarity. The polarity of electrode 28 in central channel 12 can have either a positive or negative polarity when the electrodes (30 and 32) in the second and third channels are grounded. In this mode, it is possible to add or remove anions or cations for example when the central channel has a positive polarity for the applied potential, cations will be driven out of this channel via the cation exchange membrane while anions will be added into the central channel via the anion exchange membrane. When the polarity of the central channel is changed to a negative polarity for the applied potential, cations will be added into the central channel while anions will be driven out of the central channel.

It is also possible to program the polarity of the applied potential so that removal and addition can occur on the same device. For example the pH generation could be extended by pursuing a reversed polarity configuration for a short duration followed by a normal polarity configuration. In this case all channels are supplied with electrolyte solutions. Thus, by manipulating the applied polarity and magnitude of the two currents, it is possible to manipulate the buffer concentration and pH.

As set forth in FIGS. 1 and 2, electrolyte flows through channel 22 and channel 26 with water flowing through central buffer generating channel. In this embodiment, electrode 30 has a more positive potential than electrodes 28 and 32. Also, as set forth above, the buffer generator can also include flowing various solutions through the three channels and adding or subtracting one or more ions in the central channel, by precise control of the current level in each of the two electrical circuits and the differences in the current levels, to prepare a buffer solution. In one embodiment, the feed solution to the central channel is a buffer solution and the solution exiting the channel is a modified buffer solution. In one example of this embodiment, the central channel feed solution is an electrolyte buffer and the feed to the anode and cathode channels is deionized water. The amount of cations and/or anions removed into the outside channels is precisely controlled by the two electric currents. One example of this system uses a central channel feed solution of $NaH_2PO_4$ and the anode channel is fed with NaOH and the cathode channel is fed with deionized water. The modified buffer solution exiting the central channel is a buffer including $NaH_2PO_4$ and $Na_2HPO_4$. Here the sodium was supplied from the anode channel into the central product channel containing $NaH_2PO_4$ while hydroxide is supplied via the anion exchange membrane and the cathode. The addition of NaOH into the $NaH_2PO_4$ stream could be controlled by the applied current and dictates the pH in the central product channel.

Similarly, it is also possible to bring in an anion via the cathode channel. If in the above example if the cathode channel 22 was fed with methane sulfonic acid (MSA) then the acid anion would be available for manipulating the pH of the central channel 12. In the above example if KOH was replaced with DI water the MSA could increase the acidity in the central product channel 12. It should also be noted that the two power supplies could have different current gradients thereby providing better control of the pH and ionic strength of the product channel. The sodium is supplied from the anode channel 26 into the central product channel 12 while hydroxide is supplied via the anion exchange membrane 16 and the cathode. The addition of NaOH could be controlled by the applied current and dictates the pH in the central product channel 12.

In another embodiment, deionized water flows in one of the outside channels 22 and 26 and an electrolyte solution including a source of anions or cations flows in the other one. For example, a source of cation, e.g. $Na^+$ can be used as a feed solution for the anode channel and deionized water can be used as the feed solution for the cathode channel. Alternatively, deionized water can flow through the anode channel and a source of anion, e.g., MSA, can flow in a buffer solution or other salt or an acid. Here, the feed solution to channel 22 can be a salt solution, such as a buffer solution, or an acid or a base including the anion desired to be added to the feed solution in the central channel 28 to produce the product buffer exiting channel 28. It is also possible to add a salt in the above configuration the purpose of which is to alter the ionic strength of the product stream. For example if the channel close to the anode is fed with KOH and the cathode channel is fed with MSA it would be possible to make KMSA salt in the central channel.

To summarize, deionized water or an electrolyte source of cation or anion can be fed to one or more of the three channels under control of the two electric circuits to produce a buffer of the desired pH and concentration.

Figure 3A:
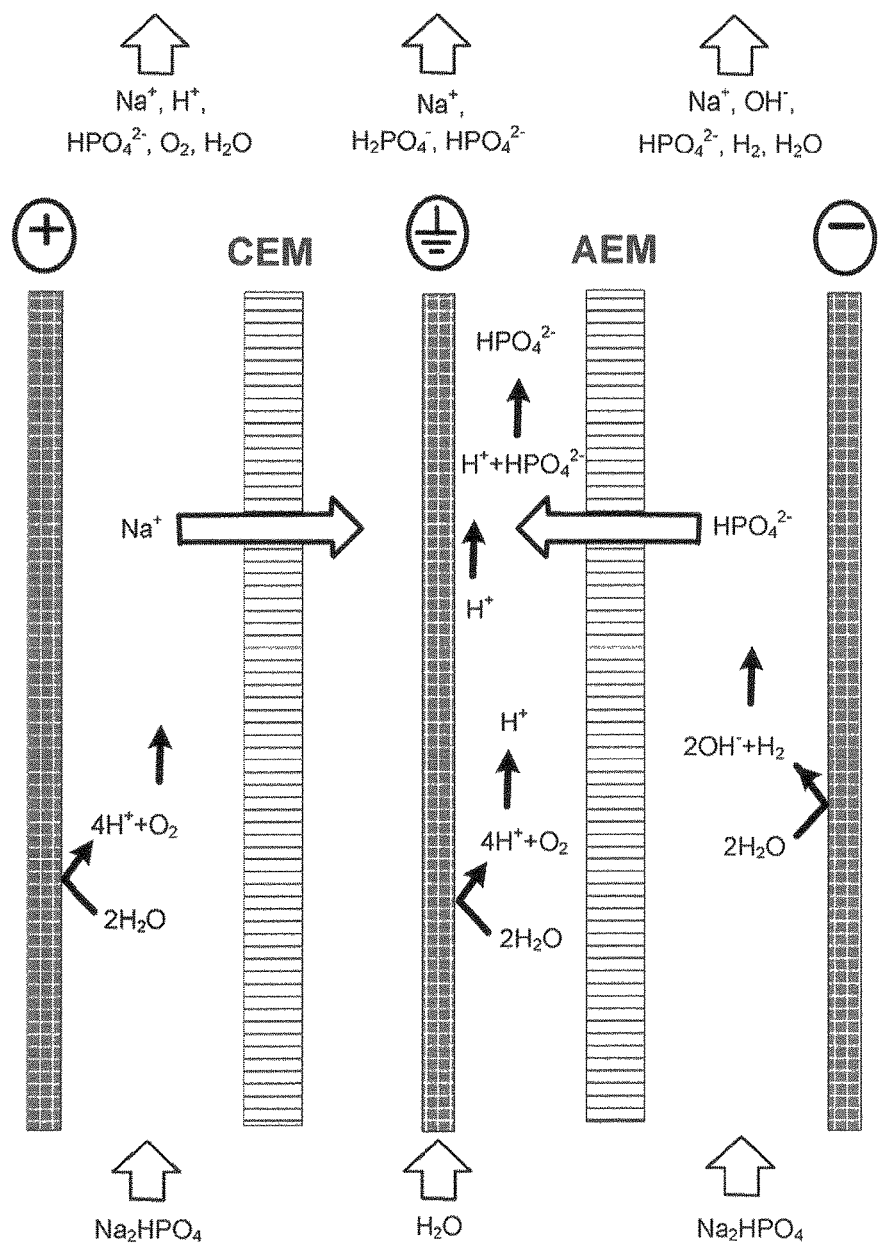
FIG. 3(a) schematically illustrates reaction schemes using the buffer generator of FIG. 1 in which water is fed to the buffer generating channel while electrolyte is fed to the outside channels and the CEM current is less than the AEM current.
Figure 3B:
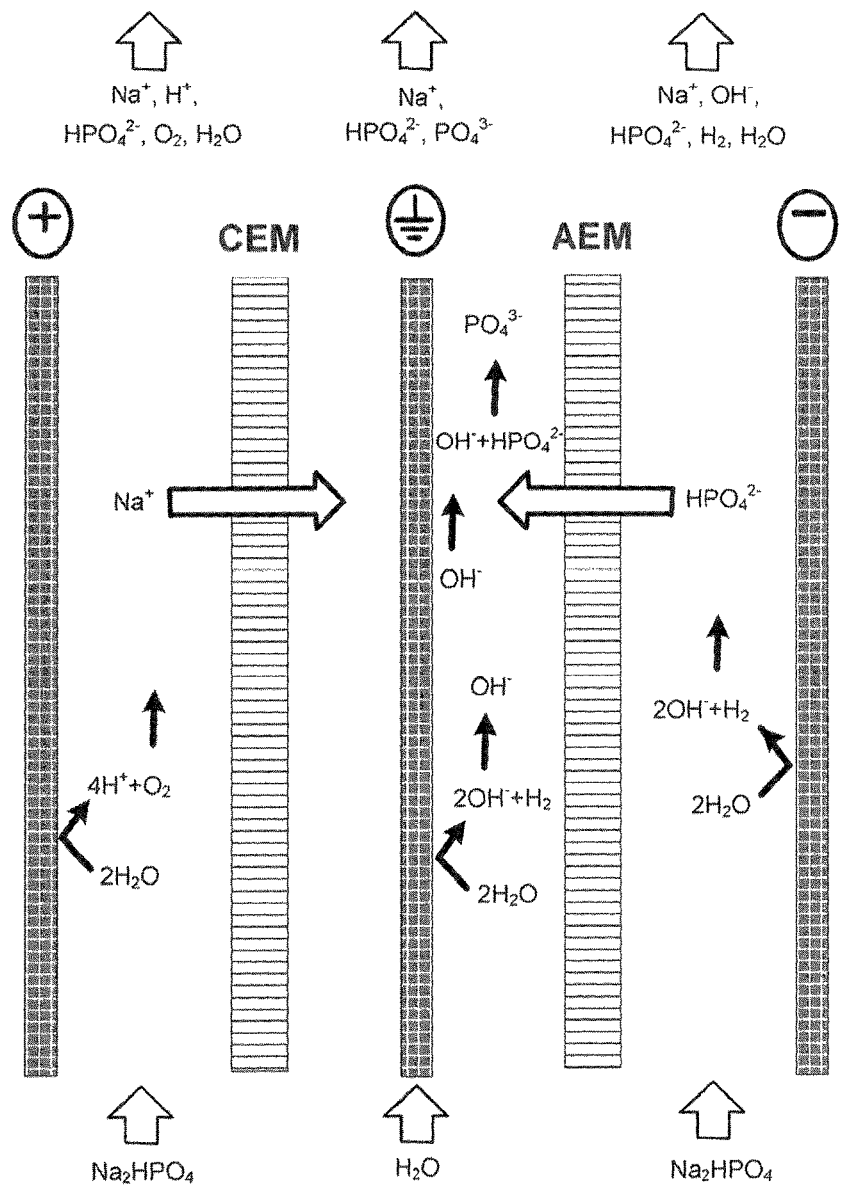
FIG. 3(b) schematically illustrates reaction schemes using the buffer generator of FIG. 1 in which water is fed to the buffer generating channel while electrolyte is fed to the outside channels and the CEM current is greater than the AEM current.

FIG. 3(a) illustrates a buffer generator with $Na_2HPO_4$ as a feed solution with a CEM current that is less than the AEM current. The reactions are shown in FIG. 3(a) when a CEM current is less than the AEM current. FIG. 3(b) illustrates the same system except that the CEM current is greater than the AEM current.

Figure 4A:
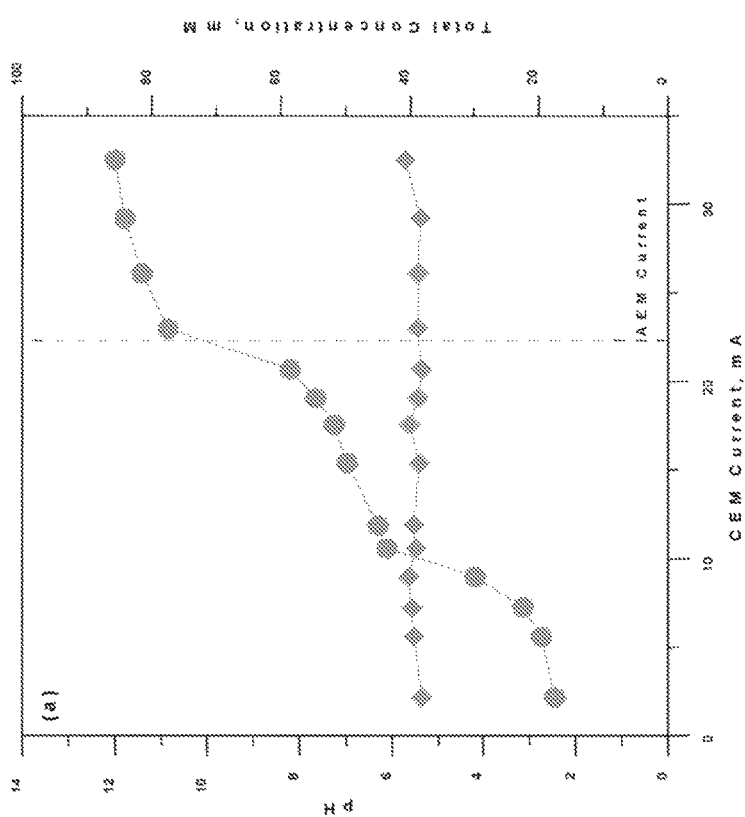
FIG. 4(a) illustrates a total buffer concentration and pH as a function of CEM current when AEM current is held constant. The dashed line indicates the AEM current and it intersects the curve where the two currents are equal. The diamond symbol represents the total buffer concentration and the ellipse symbol represents pH.

FIG. 4(a) illustrates the total buffer concentration and pH as a function of the CEM current when the AEM current is held constant. The buffer generating device outputs buffer with a modified pH by changing a magnitude of the CEM current as a function of time. In an embodiment, the modified pH can include a gradient pH. The AEM current can be approximately constant as a function of time causing the outputted buffer to have an approximately constant total buffer concentration.

Figure 4B:
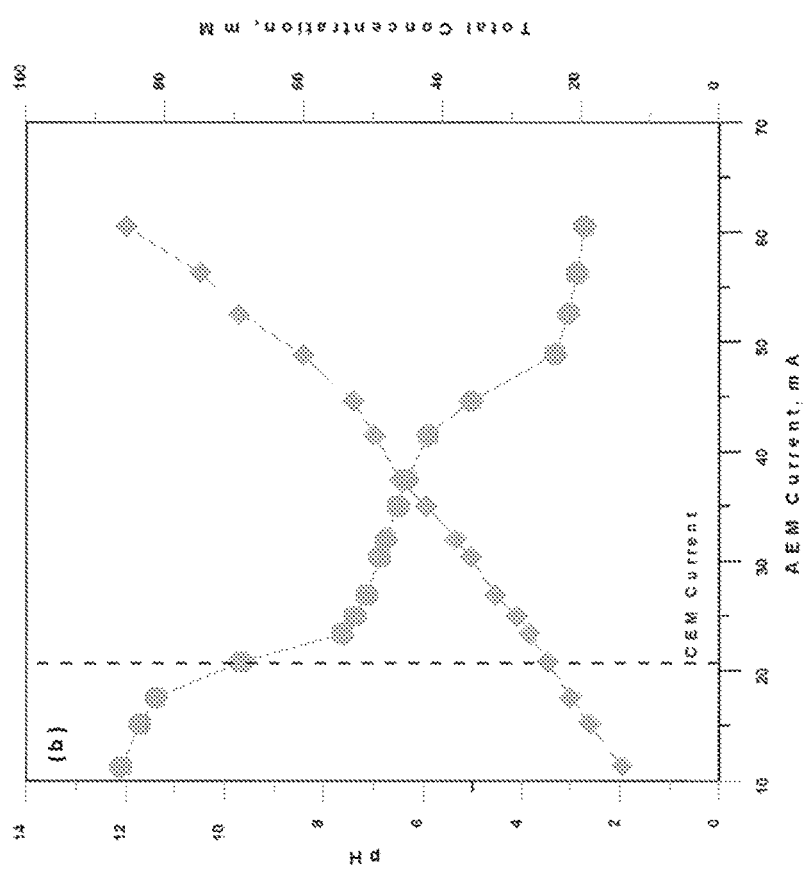
FIG. 4(b) illustrates a total buffer concentration and pH as a function of AEM current when CEM current is held constant. The dashed line indicates the CEM current and it intersects the curve where the two currents are equal. The diamond symbol represents the total buffer concentration and the ellipse symbol represents pH.

FIG. 4(b) illustrates the total buffer concentration and pH when AEM current is varied and CEM current is held constant. The buffer generating device outputs buffer with a modified buffer concentration by changing a magnitude of the AEM current. In an embodiment, the modified buffer concentration can include a gradient buffer concentration.

Referring back to FIG. 4(a), the dashed line indicates the AEM current and it intersects the curve where the two currents are equal. Similarly, in FIG. 4(b), the dashed line indicates the CEM current and it intersects the curve where the two currents are equal. The generated buffers were collected. The total buffer concentration was determined by ion chromatography. The pH was measured off-line. The central channel had a flow of water at 0.25 mL/min. The CEM side outer channel had a flow of 0.5 M $K_2HPO_4$ at 1.5 mL/min. The AEM side outer channel had a flow of 0.5 M $K_2HPO_4$ at 3.0 mL/min.

Figure 5A:
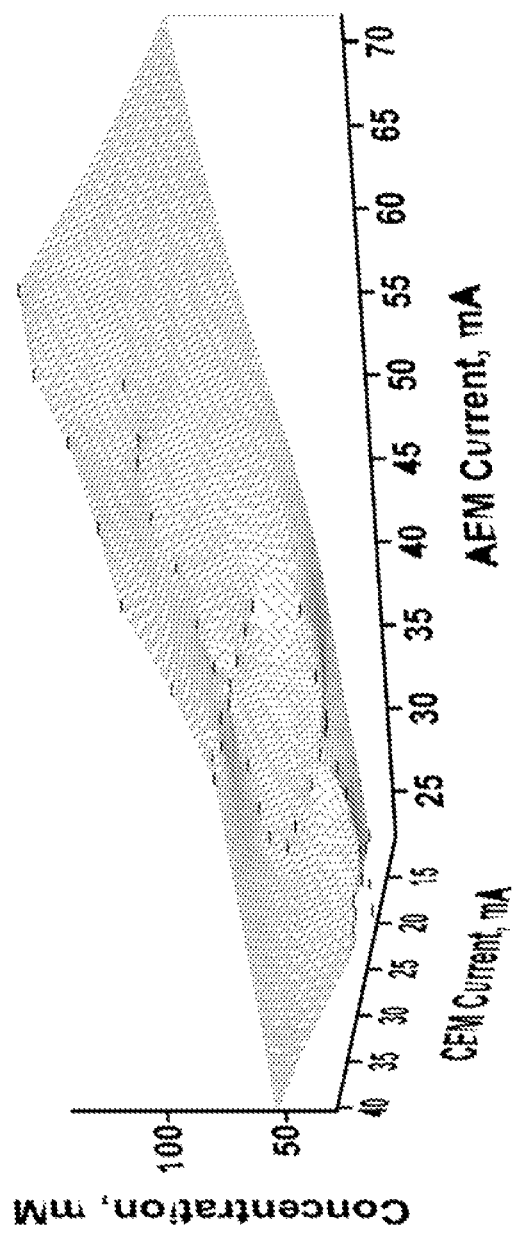
FIG. 5(a) is a three-dimensional contour graph showing the total buffer concentration as a function of the AEM current and the CEM current using the buffer generator of FIG. 1.
Figure 5B:
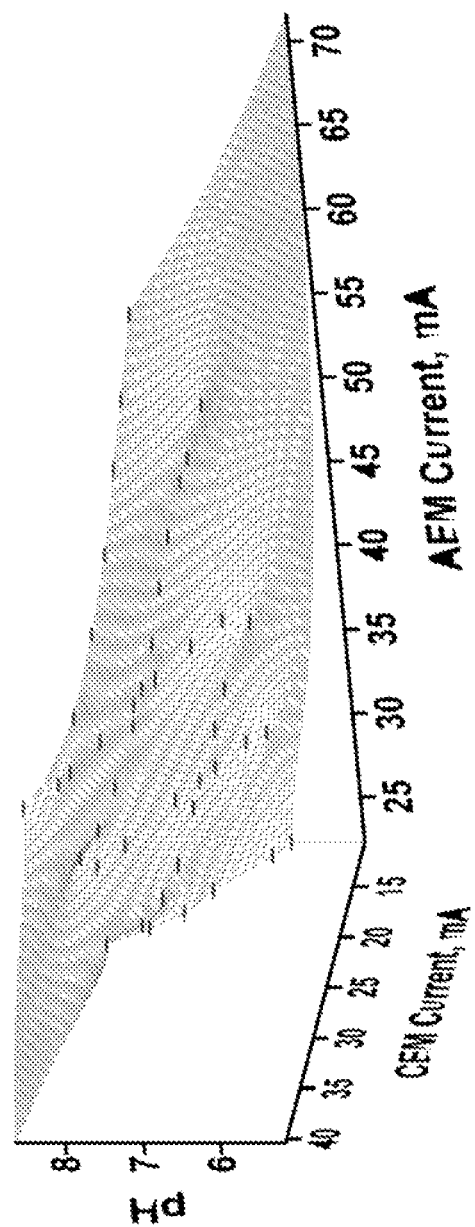
FIG. 5(b) is a three-dimensional contour graph showing the pH as a function of the AEM current and the CEM current using the buffer generator of FIG. 1.

FIG. 5(a) illustrates the total phosphate concentration generated by the system of FIGS. 3(a) and 3(b). FIG. 5(b) illustrates the pH as a function of the applied currents. The generated buffers were collected. The total buffer concentration was determined by ion chromatography. The pH was measured off-line. The central channel had a flow of water at 0.25 mL/min. The CEM side outer channel had a flow of 0.5 M $K_2HPO_4$ at 1.5 mL/min. The AEM side outer channel had a flow of 0.5 M $K_2HPO_4$ at 3.0 mL/min.

Figure 6:
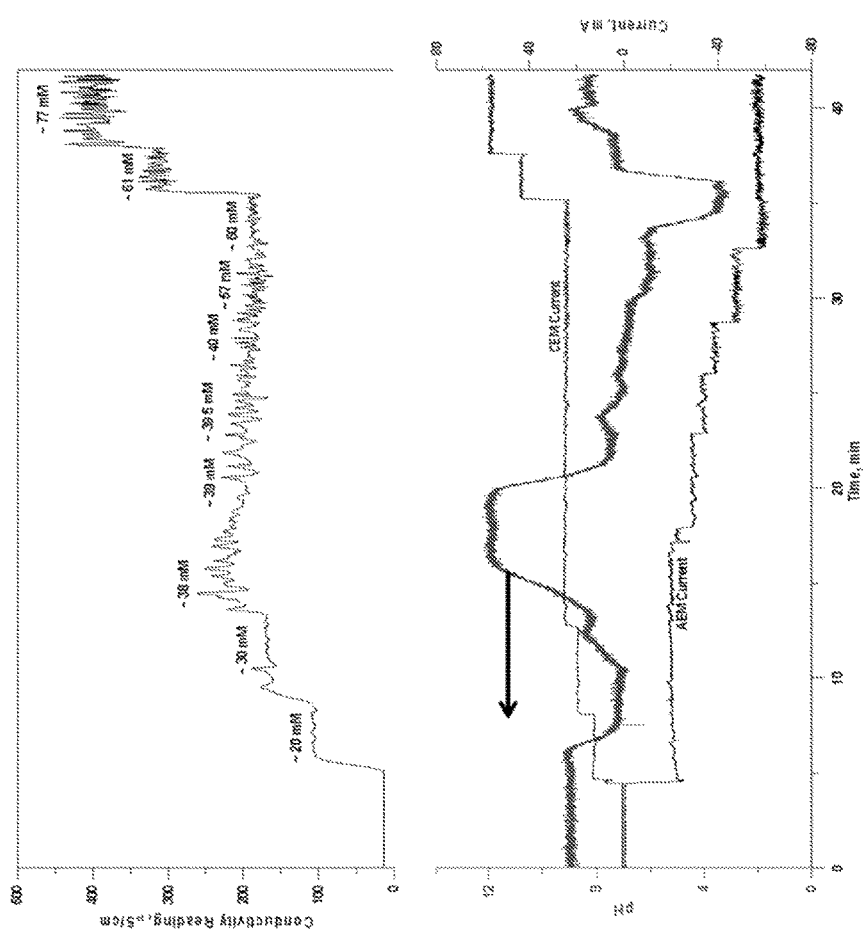
FIG. 6 illustrates the in-line conductivity and pH as the AEM current and CEM current are varied as a function of time.

FIG. 6 illustrates in-line conductivity and pH measurement as the currents were varied as a function of time. A custom built conductivity cell and pH flow cell were used. The central channel had a flow of water at 0.25 mL/min. The CEM side outer channel had a flow of 0.5 M $K_2HPO_4$ at 1.5 mL/min. The AEM side outer channel had a flow of 0.5 M $K_2HPO_4$ at 3.0 mL/min. Numerical buffer concentration values can be ascribed to sections of the conductivity time transient of FIG. 6. The buffer concentration values denoted on FIG. 6 can be determined based on a prior calibration where a plurality of conductivity measurements are collected using a range of buffer concentrations.

The following non-limiting examples are illustrative of the present invention.

EXAMPLE 1

Disodium hydrogen phosphate heptahydrate and sodium citrate dihydrate was purchased from Mallinckrodt. Ethylenediamine dihydrochloride was purchased from Acros Organics. Tris(hydroxymethyl)aminomethane hydrochloride and dipotassium hydrogen phosphate was purchased from J. T. Baker. All the chemicals are reagent grade and solutions were prepared with 18.2 MΩ·cm Milli-Q (Millipore) deionized water.

The ion-exchange membranes and the electrodes are sandwiched between two Plexiglas blocks which are of dimension of 120 mm×42.4 mm×10 mm, and provides the inlets and outlets of the flows, as well as the access of the electrodes. A 250 μm deep and 2 mm wide channel is engraved on the central inner surface of each the Plexiglasses to form the outer channel flow conduit while the central channel is provided by a cut-through channel on a 250 μm thick polypropylene sheet. 250 μm diameter platinum wires are placed inside each channel as electrodes. To prevent the electrodes in direct contact with membranes, four gasket-screens are placed between electrodes and membranes. The gasket-screens were hand-made with 290 μm thick ethylene tetrafluoroethylene (ETFE) monofilament screening fabrics (Fluortex, 250 μm mesh opening) with gasket pressed into both sides of the mesh, leaving a portion of the screen not covered by the gasket defining the fluidic pathway. A scheme is shown as follows: Electrode(+)|Gasket-Screen|CEM|Gasket-Screen|Electrode(GND)|Gasket-Screen|AEM|Gasket-Screen|Electrode(−)

With the custom built buffer generator, water was delivered by pump from ICS2000 ion chromatograph at 0.25 mL/min through the central channel; two independent streams of concentrated electrolyte solutions are delivered by purified air through the two outer channels separately. The device was placed vertically with all the three streams flowing from bottom to top to facilitate the gas escape.

Two identical custom built bipolar current sources were used to supply current across CEM and AEM, respectively. Current through the system was measured over a parallel of two 10Ω resistors connected in series with the buffer generator, and recorded via an acquisition card (USB-1408FS, Measurement Computing) and DAQ software, without any signal filtering. Two independent multimeters (Meterman) were used to monitor and verify the CEM and AEM currents, respectively.

A custom built conductivity cell with a cell constant of 6390.8 $cm^{-1}$ powered by Dionex CD25 conductivity detector was used to monitor the generated solution. A pH meter (Orion Research, model 601A) equipped with a Symphony epoxy refillable pH electrode (VWR) was used to measure the pH of the solution. The determination of generated concentration and pH was conducted in two ways. One is collecting the generated solution and then measuring the pH of each isolated solution separately. The collected solution was diluted and injected into ICS2000 system to determine the exact total concentration of the generated species. The other way is to measure the conductivity in line with the custom built cell, followed by a custom built pH flow cell to measure the pH in line. A carbonate removal device (CRD 200, Dionex) with regenerant channel inlet and outlet connected to vacuum was connected between the buffer generator and the conductivity cell for degassing. For conductivity measurement, standard solutions made of components of the buffer at varied ratios were used to calibrate the custom built conductivity cell. The pH flow-cell was made with a 5-ml plastic syringe (Luer-Lok), whose major part was removed, leaving the needle end about 1.2-cm length snugly accommodating protective teeth round the bulb of the electrode. With the pH electrode vertically placed, the solution coming out of the conductivity cell passed through a connector into the bottom of the syringe, flushing against the bottom of the bulb. The gap between the syringe and the protective teeth around the bulb allows the fluid to exit to the waste. The result of in-line pH measurement was compared to the off-line measurement and it indicated that there was no interference to reference potential of the pH meter and the reading was reasonably correct.

In the buffer generator, the applied current was used to generate $H^+$ and $OH^-$ at the electrode compartments and drive the $H^+$ or $OH^-$ through the CEM or AEM, in turn removing the cations or anions in the feeding solution. With the three-electrode buffer generator, however, the buffer itself is generated electrodialytically. The total concentration can be increased by increasing the two currents, and the difference between the two currents will dictate the pH. The scheme is shown in FIG. 2.

The origin of variation of pH is discussed as follows. If the electrons flowing from cathode next to AEM are to continue moving through central ground to anode next to CEM, when CEM current is exactly the same as AEM current, there will be no reaction taking place at the central grounded electrode. To verify it, the gas evolution was monitored when one current was kept constant while the other was varied from lower to higher relative to the constant one, using an inverted water filled 10-ml graduated cylinder. It was found that the gas volume consistently first decreased then increased with increasing current, and the minimum volume was observed when the two currents were almost identical. Therefore, it demonstrates that when CEM current is larger, there will be $OH^-$ and $H_2$ generated in the central compartment, and larger AEM current will result in $H^+$ and $O_2$. When the currents from both sides are equal, there will be no excess of $H^+$ or $OH^-$ and no gas evolution in the central compartment, and there will be equivalent cations and anions across CEM and AEM respectively. In short, the amounts of cations and anions from the feeding solution are directly proportionally to the absolute values of CEM and AEM current respectively; the amounts of either $H^+$ or OFF are decided by the difference between the two currents. And different from suppressors, with this three-electrode device, buffer is generated with gas. The scheme is shown in FIG. 3, using phosphate buffer as an example.

Phosphate buffer, one of the most commonly used buffers, is chosen to demonstrate the operation principle of the buffer generator. Considering that the typically used pH range of phosphate buffer lies in 5-8, where either $NaH_2PO_4$ or $Na_2HPO_4$ is dominant species, and $Na_2HPO_4$ provides higher conductivity, 0.5 M $Na_2HPO_4$ was chosen as the feeding solution in both of the outer channels. As predicted, with AEM current held constant, the increasing CEM current brings in increasing amount of $OH^-$, which reacts with $HPO_4^{2-}$, shifting the fraction of each species in the solution and leading to an increase in pH. The curve of pH vs. CEM current resembles the titration curve generated with titrating phosphoric acid with a strong base. Note that the amounts of phosphate anion that are driven into the central channel are dictated by the AEM current, therefore the total phosphate concentration stays almost constant (FIG. 4 (*a*)). On the other hand, when CEM current is constant and AEM current is varied, we observe the reverse titration curve which resembles titrating strong base with phosphoric acid. The concentration of the total phosphate ions increases linearly with the increasing AEM current, as predicted. We further examined the device behavior with higher applied currents with pH only limited to 6-8. A 3-D plot of concentration as a function of two currents and a 3-D plot of pH as a function of two current are shown as FIGS. 5 (*a*) and (*b*). It demonstrates that the device is capable of delivering phosphate buffer of concentration up to more than 140 mM.

EXAMPLE 2

The device of FIG. 7 is used in this example. A 50 mM potassium citrate and 50 mM ethylene diamine sulfate is fed into the buffer generating channel 12 as a source stream at a flow rate of 0.5 mL/min. Deionized water is pumped into channels 22 and 28 at a flow rate of 0.5 mL/min. A current program that allowed application of a current gradient from 10 to 50 mA is applied to the AEM membrane side and a current gradient of 50 to 10 mA is applied to the CEM membrane 14 side. The net effect of the applied current is a change in the pH of the influent source stream. In order for the buffer generator to be practical in flow application, especially in chromatography, it is required to produce a gas-free buffer in-line. As set forth below, using a degasser, the buffer with reasonable concentration can be produced without the interference from gas. A Dionex CRD 200, typically employed in suppressed ion chromatography to remove carbon dioxide from the suppressed eluent stream. The device is constructed with gas permeable membranes which allow diffusion of carbon dioxide to diffuse out from the stream. A countercurrent flow of basic solution is usually applied to the regenerant channel to assist the carbon dioxide transfer. Considering the gas to remove in the buffer generator is a considerable amount of either $H_2$ or $O_2$, a basic solution is not particularly helpful, we applied vacuum directly supplied from the hood installed in the lab to the regenerant channel. The CRD 200 was connected at the outlet of the central compartment, followed by a custom built conductivity cell in series with a custom built pH flow cell. The pH electrode itself has a certain response time, thus the conductivity signal is an indication for the speed of the response. Considering the CRD 200 and the connection tubing between the buffer generator and the conductivity cell, the response time is relatively short. The noise in the conductivity signal observed to be higher at high current might be due to disturbance from the higher current signals, and the fluctuation of generated concentration due to the increased interference from the increasing gas evolution. Due to the construction of the device, the resistance in the CEM side outer channel was larger than the AEM side outer channel, the flow rate in the CEM outer channel was limited by the pressure. The conductivity and pH signal as a result of varying currents over the time is shown in FIG. 6.

Based on the foregoing, electrodialytic generation of a buffer is illustrated. The concentration and pH can be either increased or decreased, which provides a buffer concentration or pH gradient without employing a gradient pump.

It should be noted that while in all the embodiments we talk about generating a pH gradient in the central product channel, it is also possible to use the modified regenerant stream in either the anode or cathode channels to accomplish this aspect. In this work we have shown utility of a three channel device, it is conceivable to add additional channels to accomplish the same goal of pH generation.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An electrodialytic method of generating a buffer using an electrodialytic buffer generator comprising a flow-through central buffer-generating channel comprising a first electrode, having an inlet and an outlet; a second chamber comprising a second electrode and a second aqueous liquid; a third chamber comprising a third electrode and a third aqueous liquid; a cation exchange barrier, capable of passing cations but not anions and of blocking bulk liquid flow, disposed between said second chamber and said buffer-generating channel; an anion exchange barrier, capable of passing anions but not cations and of blocking bulk liquid flow, disposed between said third chamber and said buffer-generating channel; said method comprising:
   (a) flowing a first aqueous liquid into said flow-through central buffer-generating channel, where at least one of said first, second, or third aqueous liquids comprises an aqueous electrolyte solution that includes anions or cations, or both;
   (b) passing a first current between said first and second electrodes; and
   (c) passing a second current between said first and third electrodes, whereby a buffer solution is generated in said buffer-generating channel.

2. The method of claim 1 in which said first current is greater than said second current.

3. The method of claim 1 in which said second current is greater than said first current.

4. The method of claim 1 in which said aqueous electrolyte solution comprises a strong base salt of a multiprotic acid.

5. The method of claim 1 in which said aqueous electrolyte solution comprises a strong acid salt of a multiprotic base.

6. The method of claim 1 further comprising: introducing said aqueous electrolyte solution into an inlet of at least one of said second or third chambers.

7. The method of claim 1 in which said first aqueous liquid is a deionized water.

8. The method of claim 1 in which said first aqueous liquid comprises an electrolyte solution that flows into said buffer-generating channel.

9. The method of claim 8 further comprising: introducing said second aqueous liquid into an inlet of said second chamber, in which said second aqueous liquid is a deionized water.

10. The method of claim 1 in which said first electrode is grounded.

11. The method of claim 1 in which said second and third electrodes are grounded.

12. The method of claim 1 in which said aqueous electrolyte solution flows through said second and third chambers, where each chamber includes an inlet and an outlet.

13. The method of claim 1 further comprising:
(d) outputting said buffer from said buffer-generating channel with a modified pH by changing a magnitude of said first current.

14. The method of claim 13 in which said modified pH includes a gradient pH where the first current is changed as a function of time, said method further comprising:
(e) holding said second current to be approximately constant as a function of time causing said outputted buffer to have an approximately constant total buffer concentration.

15. The method of claim 1 further comprising:
(d) outputting said buffer from said buffer-generating channel with a modified buffer concentration by changing a magnitude of said second current.

16. The method of claim 15 in which said modified buffer concentration includes a gradient buffer concentration where the second current is changed as a function of time.

17. The method of claim 1 further comprising:
(d) degassing said generated buffer solution with a gas removal device.

* * * * *